United States Patent [19]

Maruyama et al.

[11] Patent Number: 5,547,857

[45] Date of Patent: Aug. 20, 1996

[54] PROCESS FOR PRODUCING 5-METHYLURIDINE AND PURIFICATION BY SEDIMENTATION VELOCITY

[75] Inventors: Shogo Maruyama; Satoshi Kumon, both of Kawasaki, Japan

[73] Assignee: Ajinomoto Co., Inc., Tokyo, Japan

[21] Appl. No.: 422,946

[22] Filed: Apr. 17, 1995

[30] Foreign Application Priority Data

Apr. 18, 1994 [JP] Japan .................................. 6-078783

[51] Int. Cl.⁶ .......................... C12P 19/38; C07H 19/00
[52] U.S. Cl. ...................... 435/87; 435/822; 536/27.12
[58] Field of Search .................. 435/87, 822; 536/27.12

[56] References Cited

U.S. PATENT DOCUMENTS

| | | | |
|---|---|---|---|
| 4,381,344 | 4/1983 | Rideout et al. | 435/87 |
| 5,258,301 | 11/1993 | Yamauchi et al. | 435/252.5 |
| 5,384,251 | 1/1995 | Yamauchi et al. | 435/87 |

FOREIGN PATENT DOCUMENTS

| | | |
|---|---|---|
| 1320995 | 12/1989 | Japan . |
| 6128280 | 5/1994 | Japan . |

*Primary Examiner*—Michael G. Wityshyn
*Assistant Examiner*—S. Saucier
*Attorney, Agent, or Firm*—Oblon, Spivak, McClelland, Maier & Neustadt, P.C.

[57] ABSTRACT

The present provides a process for obtaining high-purity 5-methyluridine crystals from nucleic acid ingredients as starting materials using a microorganism. The process comprises culturing a microorganism, removing part or the whole of the culture medium ingredients, conducting the enzyme reaction by the microorganism, crystallizing 5-methyluridine formed, and separating the obtained crystals from other impurity crystals on the basis of a difference in the precipitation rate.

2 Claims, No Drawings

PROCESS FOR PRODUCING 5-METHYLURIDINE AND PURIFICATION BY SEDIMENTATION VELOCITY

BACKGROUND OF THE INVENTION

1. Field of the Invention

The present invention relates to a process for producing 5-methyluridine, a material useful as a synthetic intermediate for medications such as azidothymidine, a commercially available AIDS medication, and d4T (2',3'-dihydroxy-2',3'-dideoxythymidine), a medication which is undergoing clinical testing for treatment of AIDS.

2. Discussion of the Background

Currently, 5-Methyluridine is chemically synthesized and purified via crystallization from an organic solvent such as methanol, ethanol or the like (see for example, *J. Am. Chem. Soc.*, vol. 78, p. 2117 (1956); Japanese Laid-Open Patent Application (Kokai) No. 63–63668; *Helvetica Chimica Acta*, p. 2179 (1980) and *Synthesis*, p. 259 (1982)).

5-methyluridine can also be produced by reacting a nucleoside or ribose-1-phosphoric acid with 5-methyluracil in the presence of a microorganism (Japanese Laid-Open Patent Application (Kokai) No. 2-23882 (hereinafter JP 2-23882)). However, this patent does not describe how to purify 5-methyluridine and is therefore insufficient for the production of 5-methyluridine as the main product.

It is desirable to form large crystals of 5-methyluridine via crystallization so as to increase the separability of the crystals, reduce a size of the device required for the separation and improve the separation from the impurities. However, there is no teaching in JP 2-23882 to describe the same.

Ordinarily, crystal growth is influenced by the extent of supersaturation, by large particle diameter and by impurities. The composition of the impurities varies greatly depending on the system to be crystallized. Controlling the composition of the impurities is important in making crystallization possible. The specific control needed in any given system varies.

Thus, with respect to the formation of 5-methyluridine using a microorganism, although JP 2-23882 describes how to produce 5-methyluridine, it fails to describe how to purify 5-methyluridine from the reaction solution.

When 5-methyluridine was crystallized from the reaction solution of JP 2-23882 by concentration after slight pretreatment, it was found that 5-methyluridine crystals having a particle diameter of just from 20 to 30 micrometers (μm) were obtained, which decreased the separation rate and increased the size of the separator. It was further found that crystals having such a particle diameter cannot be suitably separated from impurities on the basis of a difference in the particle diameter of crystals which will be described later.

Generally speaking, in order to obtain crystals having a uniform particle diameter industrially, a method is adopted in which the fluid to be crystallized is allowed to flow by itself from a lower portion, crystals having a large diameter are divided into a lower portion, crystals having a small diameter are divided into an upper portion, and the fine crystals in the upper portion are dissolved outside the system and recycled. However, processes in which product crystals are separated from impurity crystals based on the difference in a precipitation rate (sedimentation velocity) as in the present invention are few. This is because there is no system having such a particle diameter distribution; a system in which as impurity crystals are included in product crystals, and even if the product crystals can be separated from the impurity crystals, the purity would not increased; and even if crystals have a particle diameter or qualities that enable classification, nobody has yet arrived at a classification system.

When 5-methyluridine is produced from nucleic acid ingredients as starting materials via an enzyme reaction using a microorganism, the reaction product contains unreacted nucleic acid ingredients and nucleic acids formed as by-products. When 5-methyluracil and guanosine are used as starting materials to produce 5-methyluridine, thymine, guanine, guanosine and 2-amino-7-β-ribofuranosyl-7H-purine-6(1H) one (pseudoguanosine) mainly exist as impurities in the reaction solution. Of these, for example, thymine is similar to 5-methyluridine with respect to a pattern of a change in a solubility relative to temperature and pH. Therefore, it is difficult to remove thymine via crystallization. Further, thymine is similar to 5-methyluridine with respect to the ionization pattern as well. Therefore, it is difficult to remove thymine via treatment with an ion-exchange resin.

These nucleic-acid-type impurities are peculiar to a process wherein the nucleic acid ingredients are employed as starting materials and the reaction is conducted using a microorganism. Thus, ordinary knowledge cannot be utilized, nor does known literature describe a method of separating these ingredients. It is desirable to find a method for purifying 5-methyluridine from a reaction conducted using a microorganism.

SUMMARY OF THE INVENTION

Accordingly, one object of this invention is to provide a novel process wherein 5-methyluridine is produced using a microorganism with a particle diameter sufficient to give a high purity product and to enhance the efficiency of separation between the 5-methyluridine crystals and a mother liquor such that the 5-methyluridine crystals can be separated with high efficiency from the other impurity crystals in the reaction mixture.

The present inventors have now achieved this and other objects using a process in which a microorganism is cultured, 5-methyluridine is produced from nucleic acid ingredients as starting materials via an enzyme reaction, and 5-methyluridine is crystallized and separated. In particular, they have discovered that when part or the most of the culture medium ingredients of the culture solution are removed and the nucleic acid ingredients as a substrate are then added to conduct the reaction, crystals having a particle diameter of from 50 to 550 μm are obtained. This particle diameter can give a high separation rate of the crystals and allow separation from the other nucleic acid impurities based on the difference in the particle diameter which will be described later.

DESCRIPTION OF THE PREFERRED EMBODIMENTS

The present inventors have investigated the purification of 5-methyluridine. They have found that the particle diameter of the 5-methyluridine crystals obtained by the crystallization at the latter stage varies greatly depending on the treatment of the microorganism culture solution. That is, it has been discovered that when nucleic acid ingredients as a substrate are added directly to the culture solution without removing the culture medium ingredients of the culture solution and the reaction is then carried out, the particle diameter of the obtained crystals is at most from 20 to 30 μm, and that when the crystals of this particle diameter are subjected to centrifugal filtration, the separation rate is quite low which requires a large-sized device.

They have consequently discovered that when part or the most of the culture medium ingredients are removed from the culture solution and the substrate is then added to conduct the reaction, the particle diameter of 5-methyluridine crystals obtained at the latter stage is relatively large and of high quality such that they can be utilized in the purification of 5-methyluridine.

The culture medium ingredients are separated from the culture solution by decantation after the natural precipitation of the culture solution, by centrifugal separation or by filtration. By means of these procedures, the microorganism cells can be separated from the mother liquor easily and at an optional rate.

Culturing

Suitable microorganisms to be cultured include those from the Achromobacter, Acinetobacter, Aeromonas, Agrobacterium, Alcaligenes, Arthrobacter, Bacillus, Brevibacterium, Cellulomonas, Citrobacter, Corynebacterium, Escherichia, Enterobacter, Erwinia, Flavobacterium, Hafnia, Rhodococcus, Klebsiella, Kluyvera, Kurthia, Microbacterium, Micrococcus, Mycoplana, Nocardia, Planococcus, Protaminobacter, Proteus, Pseudomonas, Rhizobium, Salmonella, Sarcina, Serratia, Sporosarcina, Streptomyces, Vibrio, Xanthomonas, and Staphyrococcus genus which have an ability of producing 5-methyl-uridine from ribose-1-phosphate or a salt thereof and 5-methyl uracil. Preferred microorganisms are Arthrobacter, Cellulomonas, Flavobacterium, Klebsiella, Microbacterium, Micrococcus and Sarcina. Suitable microorganisms and culturing conditions are described in JP 2-23882.

Removing the culture media 50 to 99%, preferably about 70 to 90%, by volume of the culture medium ingredients are suitably removed prior to addition of the nucleosides. This can be achieved by any convention means such as centrifugation and decantation.

Following removal of the culture media, a buffer solution is preferably added to restore the broth to the original volume. Suitable buffers are those which maintain the pH of the broth at 5 to 8, preferably 7.

Conducting the enzyme reaction 5-methyluridine is suitable produced from either the remaining culture media or the media supplemented with buffer by adding nucleic acid ingredients as starting materials and converting them via the microorganism. Preferably, a nucleoside, inorganic phosphoric acid and 5-methyluracil (thymine) are reacted in the presence of a microorganism. Examples of suitable nucleosides include adenosine, guanosine, inosine, uridine, cytidine and xanthosine (JP 2-23882). The reaction mixture is suitably kept at a temperature of between 20°–70° C., preferably between 50°–70° C.

Following the reaction, the reaction solution is preferably cooled, filtered, decolored with activated carbon, refiltered, and concentrated in vacuo.

In this enzyme reaction, the remaining nucleosides and 5-methyluracil (thymine), the bases formed as by-products from the respective nucleosides used and phosphoric acid are present as impurities. It is easily considered that these impurities would be separated from 5-methyluridine based on the difference in solubility between the impurities and 5-methyluridine. However, the nucleic acid components are similar to each other with respect to the patterns of the solubilities relative to a temperature and pH. Therefore, it is not easy to separate these in this content.

Crystallization of 5-methyluridine

While the present inventors have studied the removal of the nucleic acid ingredients formed as by-products in the reaction solution, they have found that the crystals of 5-methyluridine become relatively large, whereas the crystals of other ingredients do not become large, and further that the precipitation rate of 5-methyluridine in the fluid is markedly high compared to that of the other crystals.

The reaction was conducted under the conditions described in JP 2-23882 by removing part or most of culture medium ingredients from a culture solution and then adding a substrate. Thereafter, the reaction solution was cooled, filtered, decolored with activated carbon and refiltered. The thus-obtained filtrate was concentrated, cooled to a temperature in the range of from 3° to 15° C. and crystallized. Among the crystals which were precipitated without adding any other solvent, the average particle diameter of the 5-methyluridine crystals was from 50 to 550 μm, while that of the impurity crystals was approximately from 10 to 30 μm.

After the 5-methyluridine crystals in the fluid were precipitated for from 5 to 10 minutes, the portion other than the layer of the 5-methyluridine crystals was allowed to flow out upon placing the container-at an incline (decantation). Further, after the crystals in the solution that flowed out were separated, the mother liquor was returned to the container, stirred and then subjected to decantation again. These procedures were repeated to obtain high-purity 5-methyluridine which contained fewer other crystals.

The time necessary for the precipitation of 5-methyluridine varies depending on the scale of the crystallization device or the particle diameter of the crystals. However, the precipitation time can be easily set by drawing out part of the crystallized sludge, actually precipitating the sludge in a messcylinder or the like, measuring the time required for the precipitation and the precipitation distance and calculating, based on these data, a precipitation rate required in the actual device.

On the other hand, since the particle diameter of the impurity crystals is always approximately constant, the precipitation time may be considered with respect to 5-methyluridine only. When the precipitation time is too long, the impurity crystals somewhat precipitate. In a small device such as a messcylinder, a precipitated layer of fine crystals is formed in approximately 30 minutes. In this instance too, the time required for the impurity crystals to precipitate can be easily calculated on the basis of the scale of the device, and the limit of the precipitation time can be determined from the calculated value.

When using an improved fluidized-bed-type continuous crystallization vessel or a fluidized-bed classification-type crystallizater can which is designed, the linear velocity of an actual device can be easily determined by passing a clear mother liquor from under the vessel, and measuring the linear velocity of a fluid necessary for allowing the impurity crystals alone to flow out without the 5-methyluridine crystals flowing out.

In case a so-called superdecanter is used, the feed rate of a fluid in an actual device can be set by using a small-sized device and measuring the feed rate of the fluid per precipitation area and the separability of the crystals.

Thus, the present inventors have found that upon utilizing the difference in the precipitation rate of crystals, 5-methyluridine can be effectively separated from the other nucleic acid ingredients.

The above-mentioned separation method is especially effective for separating thymine which can hardly be separated from 5-methyluridine. Thymine is similar to 5-methyluridine with respect to the pattern of the change in the solubility relative to temperature and pH, and the two compounds are hardly separated from each other. The two compounds are also similar to each other with respect to the pattern of ionization. Accordingly, the two compounds can hardly be separated from each other by an ion-exchange resin. Under these circumstances, the process of the present invention is quite effective for separating 5-methyluridine from thymine.

The process of the present invention is also quite effective for separating 5-methyluridine from guanosine, guanine and pseudoguanosine which are other coexistent nucleic acids.

It is uncertain why the 5-methyluridine crystals having the large particle diameter can be obtained only when part or most of the culture medium ingredients in the culture solution are removed. It is presumably because amino acids and other ingredients such as sugar which are contained in the culture medium ingredients react during the enzyme reaction and the reaction products hinder the growth of the 5-methyluridine crystals. The temperature of the reaction using the microorganism is 60° C. which is higher in comparison to that in the general productions using microorganisms. It is considered that this high temperature expedites the above-mentioned side reaction and requires the removal of the culture medium ingredients in the present invention.

In the case of 5-methyluridine, the particle diameter of the crystals of the commercial reagent is at most about 50 μm. The present inventors have recrystallized this from water, and have then obtained crystals having a particle diameter of approximately 500 μm.

On the other hand, as a result of the powder X-ray diffraction of 5-methyluridine crystals obtained from an actual solution system containing impurities, it has been found that 5-methyluridine does not form a "mixed crystal" with other impurities, and if 5-methyluridine crystals alone can be withdrawn from a blended crystal group, a high-purity product can be obtained. The particle diameter of the 5-methyluridine crystals in the actual solution system is usually from 300 to 600 μm, and from 50 to 100 μm at the smallest. At this time, the particle diameter of the impurity crystals is from 5 to 50 μm.

When a crystallized slurry is allowed to stand after stirring, 5-methyluridine crystals appear in the lower portion of the glass container and the solution in the upper portion remains turbid within a short period time. Thus, 5-methyluridine crystals can be separated from other crystals upon utilizing the difference in the precipitation rate.

One of methods in which the crystals are separated from each other based on the difference in the precipitation rate is a decantation method in which the crystallized slurry is mixed well, and is then allowed to stand, and while most of the 5-methyluridine crystals are precipitated and the other crystals float, the layers other than the 5-methyluridine layer are caused to flow out by placing the container in an inclined position. The crystal in the solution that flows out are separated. The mother liquor is returned to the original container. By repeating the above procedures several times, the 5-methyluridine crystals free from the impurity crystals can be obtained.

Since it is difficult to place the container of a large-sized device at an incline, there is no alternative but to use mechanical force. For instance, a method is considered in which a non-precipitated layer is sucked out by means of a pump or an overflow port is formed in a suitable position and after the completion of the precipitation, a solution at the upper portion overflows from the overflow port. Further considered is a method in which a general fluidized-bed-type continuous precipitation tank is improved such that a clear mother liquor flows from a lower portion of the tank and the impurity crystals alone flow out without the 5-methyluridine crystals flowing out, or a method in which large crystals and small crystals are classified at a time by means of a so-called superdecanter.

A predetermined efficiency of separation and a predetermined purity of a product can be obtained by repeating the decantation or the mechanical separation.

In either method, the efficiency of separating the impurity crystals is able to be enhanced by employing such procedures as separating the impurity crystals from a separated fluid which contains the impurity crystals by a centrifugal separator or by filtrator and returning the mother liquor to the original device.

When the layer of the separated 5-methyluridine crystals is separated via centrifugal separation or filtration and the crystals are washed with water or, if possible, with cold water, crystals having a higher purity can be obtained.

EXAMPLES

Having generally described this invention, a further understanding can be obtained by reference to certain specific examples which are provided herein for purposes of illustration only and are not intended to be limiting unless otherwise specified.

EXAMPLE 1

A culture broth of *Flavobacterium rhenanum* FERM BP-1862 was prepared according to Example 1 of JP 2-23882. The broth was centrifuged to remove 50% of the culture medium ingredients. A tris-buffer solution was added thereto to restore the broth to the original volume. 5-Methyluracil and guanosine as substrates were added to the solution, and the mixture was reacted while keeping the temperature at 60° C. The reaction solution was cooled, filtered, decolored with activated carbon, refiltered, and concentrated in vacuo. The concentrate was cooled to 5° C. The particle diameter of the crystals in the crystallized slurry was approximately 80 μm. Further, 5-methyluridine and other crystals of nucleic acid ingredients formed as impurities were separated well into two layers through natural precipitation.

EXAMPLE 2

A culture broth of *Flavobacterium rhenanum* FERM BP-1862 was prepared according to Example 1 of JP 2-23882. The broth was centrifuged to remove 90% of the culture medium ingredients. A tris-buffer solution was added thereto to restore the broth to the original volume. 5-Methyluracil and guanosine as substrates were added, and the reaction and the post-treatment were conducted in the same manner as in Example 1 of the present invention. The particle diameter of the crystals in the crystallized slurry was approximately 70 μm. Further, 5-methyluridine and other crystals of nucleic acid ingredients formed as impurities were separated well into two layers through natural precipitation.

EXAMPLE 3

A culture broth of *Flavobacterium rhenanum* FERM BP-1862 was prepared according to Example 1 of JP 2-23882. The broth was centrifuged to remove 90% of the culture medium ingredients. An inorganic phosphate buffer solution was added thereto to return the solution to the original volume. 5-Methyluracil and guanosine as substrates were added thereto, and the reaction and the posttreatment were conducted in the same manner as in Example 1 of the present invention. The particle diameter of the crystal in the crystallized slurry was approximately 100 μm. Further, 5-methyluridine and other crystals of nucleic acid ingredients formed as impurities were separated well into two layers through natural precipitation.

EXAMPLE 4

The upper layer obtained in Examples 1 to 3 was separated from the 5-methyluridine lower layer via decantation, and the lower layer was centrifuged. It was found that the lower layer could be separated at a high rate.

EXAMPLE 5

A culture broth of *Micrococcus luteus* FERM P-7399 was prepared according to Example 1 of JP 2-23882 and the washed cells were prepared. A tris-buffer solution was added thereto to restore the broth to the original volume. 5-Methyluridine and guanosine as substrates were added, and the enzyme reaction was conducted in the same manner as in Example 1 of the present invention. The obtained enzyme reaction solution was cooled, filtered, decolored with activated carbon, refiltered, and concentrated in vacuo to obtain 384.9 g of a concentrate containing 25.5% of 5-methyluridine, 1.95% of thymine and 0.57% of guanosine.

While stirring at 50 rpm, the concentrate was gradually cooled to 10° C. to precipitate crystals. The crystals were allowed to stand for 10 minutes, and a fine crystal-containing suspension in the upper portion other than a 5-methyluridine layer in the lower portion was separated by decantation and caused to flow out. The crystals in the solution that flowed out were separated by filtration to obtain 8.62 g of wet crystals containing 22.6% of 5-methyluridine, 50.7% of thymine and 10.7% of guanosine in terms of dry weight. The mother liquor was returned to the original container in which the 5-methyluridine crystal layer remained, and was stirred and recooled to 10° C. The crystals were separated again by decantation as mentioned above, and the crystals in the solution that flowed out were separated by filtration to obtain 4.57 g of crystals in a dry state containing 41.4% of 5-methyluridine, 26.1% of thymine, 14.4% of guanosine and 0.052% of guanine in terms of dry weight. The mother liquor was returned to the original container in which the layer of the 5-methyluridine crystals remained, and was cooled to 10° C. while stirring. The whole of the fluid was then separated by a basket-type centrifugal filter. At the time of the separation, the crystal layer was washed with 57.8 g of cold water. The separated crystals were dried to obtain 75.21 g of hydrated crystals. The yield of 5-methyluridine from the concentrate was 71.4%. The purity of the crystals was 93.24%, and 3.33% of thymine and 0.342% of guanosine were contained as impurities. The ratio of thymine to 5-methyluridine was 7.6% in the concentrate and 3.6% in the product, and was thus reduced by half via the precipitation and decantation steps. In addition, pseudoguanosine was notably reduced too, though it was qualitatively determined. Further, the nucleic acids formed as impurities might have been more reduced by repeating the decantation.

The average particle diameter of the 5-methyluridine crystals in the crystallization was approximately 350 μm, and the average particle diameter of the fine crystals was 10 μm.

EXAMPLE 6

A culture broth of *Micrococcus luteus* FERM P-7399 was prepared according to Example 1 of JP 2-23882 and the washed cells were prepared. A tris-buffer solution was added thereto to restore the broth to the original volume. 5-Methyluridine and guanosine as substrates were added, and the enzyme reaction was conducted in the same manner as in Example 1 of the present invention. The obtained enzyme reaction solution was cooled, filtered, decolored with activated carbon, refiltered, and concentrated in vacuo to obtain 580 liters of a concentrate containing 23.0% of 5-methyluridine, 1.71% of thymine and 0.45% of guanosine. The concentrate was cooled gradually to 5° C. in a crystallization can while stirring at 100 rpm to precipitate crystals. The stirring was stopped, and 5-methyluridine crystals were precipitated for approximately 15 minutes. Then, a fine crystal-containing suspension in an upper portion was separated mechanically by means of a pump. The fine crystals in the separated solution was separated by filtration. The mother liquor was returned to the original crystallizer can, stirred and recooled to 5° C. A series of the above-mentioned procedures, namely stirring, allowing to stand, separation of the fine crystal-containing suspension in the upper portion, separation of the fine crystals by filtration and resuspension, were repeated for a total of four times. Subsequently, the whole suspension was separated by a basket type centrifugal filter. At the time of the separation, the crystals were washed with 60 liters of water. The separated crystals were dried to obtain 96 kg of hydrous crystals. The yield of 5-methyluridine from the concentrate was 72.0%. The purity of the crystals was 93.8%, and 1.8% of thymine and 0.16% of guanosine were contained as impurities. The ratio of thymine to 5-methyluridine was 7.4% in the concentrate and 1.9% in the product, and was thus reduced to ¼ via the precipitation and decantation steps. Further, pseudoguanosine was also greatly reduced. The nucleic acids formed as impurities might have been more reduced by repeating the decantation. In this crystallization, the average particle diameter of the 5-methyluridine crystals was approximately 550 μm, and the average particle diameter of the fine crystals was 15 μm.

COMPARATIVE EXAMPLE 1

A culture broth of *Flavobacterium rhenanum* FERM BP-1862 was prepared according to Example 1 of JP 2-23882. 5-Methyluracil and guanosine as substrates were added without removing the culture medium ingredients of the strain culture solution, and were reacted while keeping the temperature at 60° C. in the same manner as in Example 1 of the present invention. The reaction solution was cooled, filtered, decolored with activated carbon, refiltered and concentrated in vacuo. The concentrate was recooled to 5° C. The particle diameter of the obtained 5-methyluridine crystals was from 20 to 30 µm. The separation phenomenon of 5-methyluridine crystals from other crystals of nucleic acids formed as impurities was not observed. Further, the centrifugal separation took much time.

COMPARATIVE EXAMPLE 2

A culture broth of *Micrococcus luteus* FERM P-7399 was prepared according to Example 1 of JP 2-23882 and the washed cells were prepared. A tris-buffer solution was added thereto to restore the broth to the original volume. 5-Methyluridine and guanosine as substrates were added, and the enzyme reaction was conducted in the same manner as in Example 1 of the present invention. The obtained enzyme reaction solution was cooled, filtered, decolored with activated carbon, refiltered and concentrated in vacuo to obtain 7.05 kg of a concentrate containing 25.2 of 5-methyluridine, 1.55% of thymine and 0.42% of guanosine. The concentrate was further cooled gradually to 5° C. while stirring to precipitate crystals. The whole of the suspension was separated directly by means of a basket-type centrifugal filter without allowing it to stand. Then, 5,223 g of a mother liquor containing 4.5% of 5-methyluridine, 0.26% of thymine and 0.12% of guanosine were obtained. Further, the crystal layer was washed with 814 g of cold water. At the time of the washing, the mother liquor contained 5.18% of 5-methyluridine, 0.31% of thymine and 0.19% of guanosine, and the amount of the mother liquor was 1,926 g. The separated crystals were dried to obtain 1.52 kg of hydrated crystals. The yield of 5-methyluridine from the concentrate was 76.3.

The purity of the crystals was 89.28%, and 5.21% of thymine and 0.69% of guanosine were contained as impurities. The ratio of thymine to 5-methyluridine was 6.2% in the concentrate and 5.8% in the product, and was thus not reduced at all via the crystallization step.

Having now fully described the invention, it will be apparent to one of ordinary skill in the art that many changes and modifications can be made thereto without departing from the spirit or scope of the invention as set forth herein.

What is claimed as new and desired to be secured by letters patent of the United States is:

1. A process for producing 5-methyluridine which comprises the steps of:

culturing a microorganism in a culture medium, removing 50–90% of said culture medium from the microorganism, adding a buffer to the microorganism, said buffer being added in an amount effective for product separation based on sedimentation velocity, reacting a nucleoside or ribose-1-phosphoric acid with 5-methyluracil in the remaining culture medium and buffer containing said microorganism, crystallizing 5-methyluridine formed, by forming 5-methyluridine crystals of average particle diameter from 50 to 550 µm, and impurity crystals of average particle diameter from 5 to 50 µm, and separating 5-methyluridine crystals from impurities based on a difference in sedimentation velocity of 5-methyluridine crystals and impurity crystals.

2. The process of claim 1, wherein said separating is conducted by decantation or mechanical separation.

\* \* \* \* \*